United States Patent
Masaki (10) Patent No.: US 7,553,282 B2
(45) Date of Patent: Jun. 30, 2009

(54) NON-CONTACT TONOMETER

(75) Inventor: Toshifumi Masaki, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 187 days.

(21) Appl. No.: 10/690,075

(22) Filed: Oct. 20, 2003

(65) Prior Publication Data
US 2004/0087849 A1 May 6, 2004

(30) Foreign Application Priority Data
Oct. 25, 2002 (JP) ............................. 2002-310972

(51) Int. Cl.
*A61B 3/16* (2006.01)
*A61B 13/00* (2006.01)
*A61B 3/00* (2006.01)
*A61B 3/10* (2006.01)
*A61B 3/14* (2006.01)

(52) U.S. Cl. .................. 600/398; 600/401; 600/405; 600/558; 351/200; 351/204; 351/210; 351/211

(58) Field of Classification Search ................ 600/398, 600/401, 405, 558; 351/200, 204, 210, 211; *A61B 3/16*
See application file for complete search history.

(56) References Cited

U.S. PATENT DOCUMENTS

| | | | | |
|---|---|---|---|---|
| 4,995,393 A | * | 2/1991 | Katsuragi et al. | 600/401 |
| 5,465,123 A | * | 11/1995 | Iijima | 351/208 |
| 5,469,233 A | * | 11/1995 | Katsuragi | 351/205 |
| 5,532,769 A | * | 7/1996 | Miwa et al. | 351/205 |
| 5,727,551 A | * | 3/1998 | Takagi | 600/399 |
| 6,190,317 B1 | * | 2/2001 | Hayafuji | 600/405 |
| 6,673,014 B2 | * | 1/2004 | Badehi et al. | 600/398 |

FOREIGN PATENT DOCUMENTS

JP 2002-172090 6/2002

OTHER PUBLICATIONS

English Language Abstract of JP 2002-172090.
Translation of Chinese Search Report and Office Action dated Jun. 17, 2005 (Computer Generated).
Translation of Japanese Patent Application JP 2002-34927 (Computer Generated).

* cited by examiner

*Primary Examiner*—Max Hindenburg
*Assistant Examiner*—Jeffrey G Hoekstra
(74) *Attorney, Agent, or Firm*—Cowan, Liebowitz & Latman, P.C.

(57) ABSTRACT

A non-contact tonometer changes a reference signal used for determining reliability of a signal indicating deformation of a cornea based on the reflectance of the cornea of an eye to be examined. Thus, the non-contact tonometer can perform stable measurement irrespective of the reflectance of the cornea of the eye to be examined.

1 Claim, 7 Drawing Sheets

NON-CONTACT TONOMETER

BACKGROUND OF THE INVENTION

1. Field of the Invention

The present invention relates to a non-contact tonometer used in an eye doctor's office etc.

2. Related Background Art

In a conventional non-contact tonometer, a piston is moved in a cylinder driven by rotation of a rotary solenoid to compress the air in the cylinder so that a compressed air is blown to a cornea of an eye to be examined (i.e. a patient's eye). At the same time measurement light is projected onto the cornea from a light source and reflection light from the cornea is received by a photo sensor or the like. Then, certain deformation of the cornea is detected by detecting a peak of the output signal from the photo sensor, and the internal pressure in the interior of the cylinder is measured. The measured pressure is converted to an intraocular pressure value.

In the case that alignment is displaced due to a failure in fixation of the eye to be examined upon measurement or in the case that eyelashes overlap the measurement field, the photo sensor cannot receive a light flux normally. In that case, the output of the photo sensor is weakened and reliability of the measurement becomes low even when a peak of the deformation signal is detected.

In view of the above, in the case that the peak of the output signal of the photo sensor is lower than a predetermined reference value, the measurement result at that time is disregarded as an error or a mark indicating low reliability is annexed to the measurement result.

However, the reflectance of the cornea of the eye to be examined differs between individuals, while a certain constant value is used as the reference value or the criterion of reliability of measurement regardless of the reflectance of the cornea. Consequently, in the case that an eye having a high cornea reflectance is examined, there is a risk that the output from the photo sensor will not becomes lower than the reference value even if misalignment or the like occurs at the time of measurement and the output is weakened. In other words, there is a risk that the measurement result could be determined as normal in spite that the reliability of the result is low in reality.

On the other hand, in the case that the reflectance of a cornea is low, since the output from the photo sensor is low, there is a risk that the output from the photo sensor will not becomes higher than the reference value and the measurement will be regarded as an error or the mark indicating low reliability will be annexed, in spite that the measurement has been normally performed.

SUMMARY OF THE INVENTION

An object of the present invention is to eliminate the above-described problems and to provide a non-contact tonometer that can stably make determination with high reliability irrespective of variations in the reflectance of eyes to be examined.

A non-contact tonometer according to the present invention that attains the above object comprises alignment detection means for projecting a light flux for alignment to the cornea of an eye to be examined and detecting the reflection light thereof, pressurizing means for blowing a fluid onto the cornea of the eye to be examined with a pressure variable with time to deform the cornea; a projection optical system for projecting a light flux for measurement to the corner of the eye to be examined, light receiving means for detecting reflected light quantity from the cornea of the eye to be examined, deformation detection means for detecting certain deformation of the cornea by detecting a peak of an output from the light receiving means, and determination means for determining reliability of measurement based on comparison of the output of said light receiving means at the peak and a reference value, wherein said reference value of reliability is changed in accordance with received light quantity of said alignment detection means.

DESCRIPTION OF THE PREFERRED EMBODIMENTS

In the following, the present invention will be specifically described based on an embodiment shown in the drawings.

Figure 1:
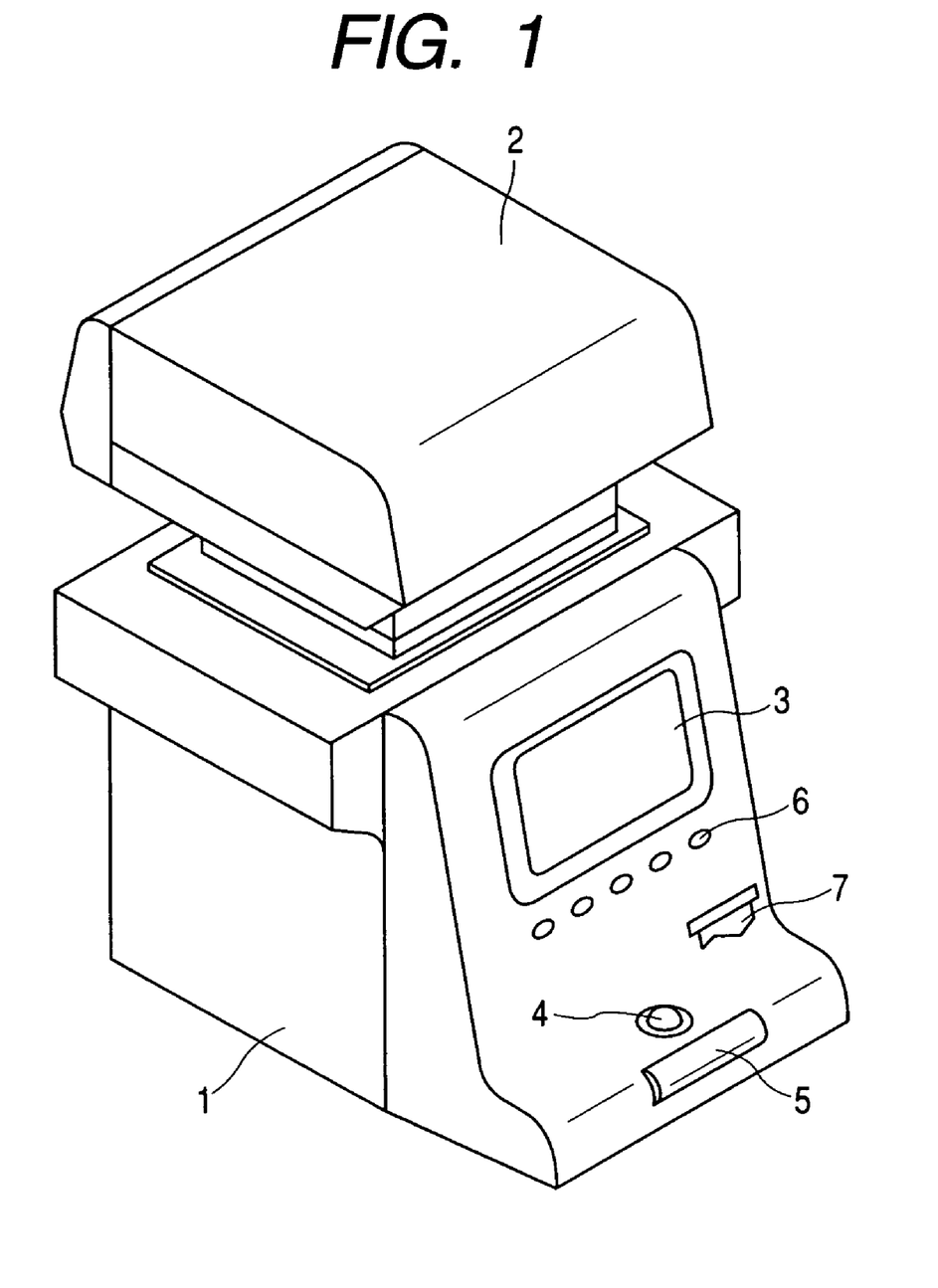
FIG. 1 is a perspective view showing the appearance of an embodiment of the present invention.

FIG. 1 shows the appearance of a non-contact tonometer. The non-contact tonometer is provided with a base 1 and a measuring portion 2 movably disposed on the base 1. On the side of the base 1 to be operated by an examiner (i.e. an operator), there is provided a monitor 3 on which measurement values and an eye to be examined etc. are displayed, a track ball 4 and a roller 5 used for roughly aligning the measuring portion 2 with the eye to be examined, a switch panel 6 in which a printing switch, a measurement starting switch and a selecting and setting switch etc. are arranged and a printer 7.

An examinee (i.e. a patient) should place his or her head on a head support portion (not shown) provided on the side opposite to the side to be operated by the examiner so that the eye to be examined is positioned in front of an objective portion of the measuring portion 2 to enable measurement. The measuring portion 2 can be moved three-dimensionally relative to the eye to be examined by drive of motors of three axes along the left-right (horizontal), up-down (vertical) and forward-backward (depth) directions so that the measuring portion can be positioned relative to the eye to be examined by electrical drive.

Figure 2:
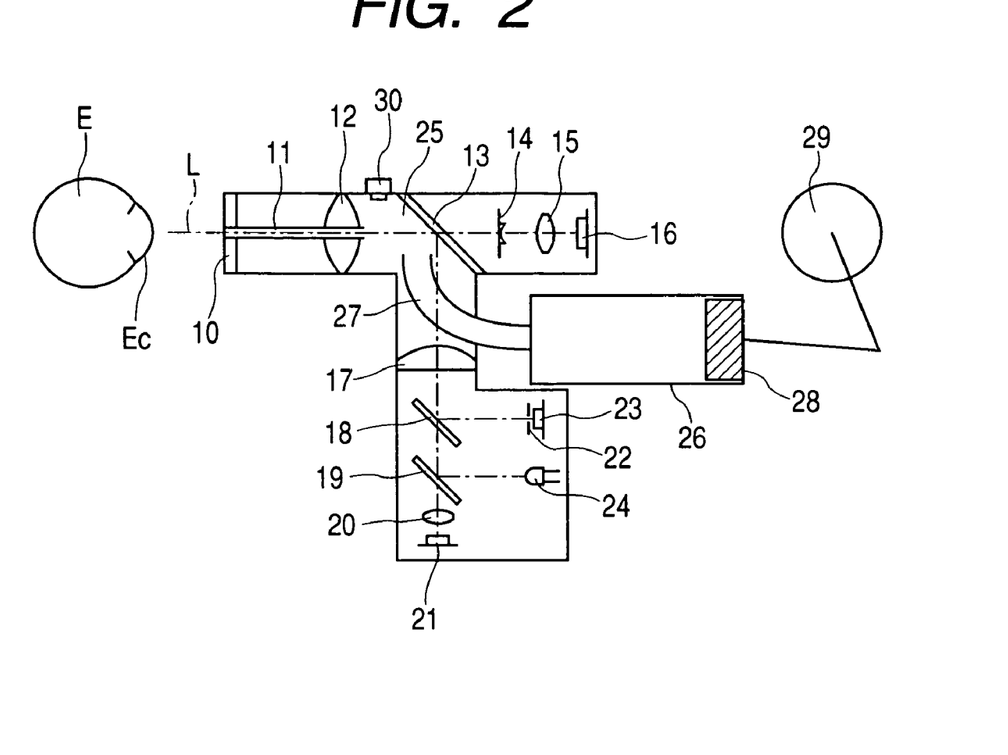
FIG. 2 is a diagram showing an optical system and a mechanical system of a measuring portion.
Figure 3:
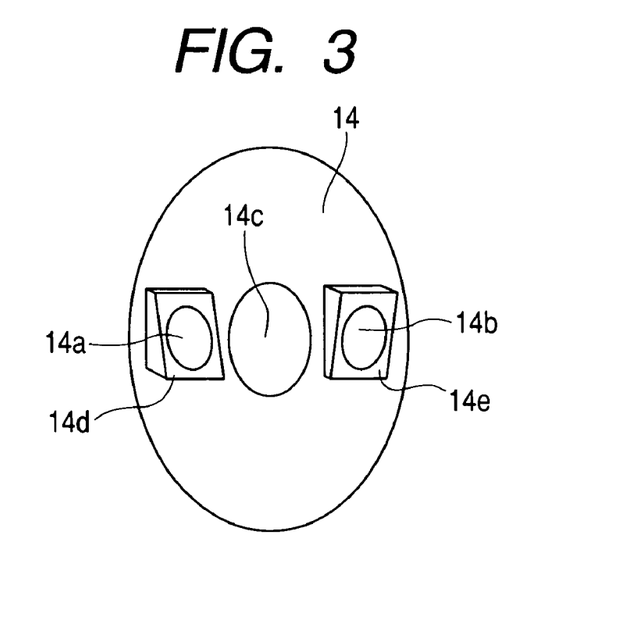
FIG. 3 is a perspective view showing an alignment prism stop.

FIG. 2 shows the internal structure of the measuring portion 2, wherein an optical system for observing the eye to be examined is disposed opposed to the eye to be examined E on an axis L. On the axis L, there is provided a window 10 having a hole, a nozzle 11, a lens 12, a dichroic mirror 13, an alignment prism stop 14 having opening portions 14a to 14c as shown in FIG. 3, a lens 15 and a CCD camera 16 in the mentioned order from the side of the eye to be examined E. The alignment prism stop 14 has prisms 14d and 14e attached to the opening portions 14a and 14b.

In the incidence side of the dichroic mirror, there is arranged a lens 17, a half mirror 18, a dichroic mirror 19, a projection lens 20 and a light source 21. In addition, in the incidence side of the half mirror 18, there is provided an aperture 22 and a photo sensor 23. In the incidence side of the dichroic mirror 19, there is provided an eye fixation LED 24.

Furthermore, a cylinder 26 is in communication with a compression chamber 25 defined by the lens 12, the dichroic mirror 13 and the lens 17 via a tube 27. The piston 28 of the cylinder 26 is adapted to be driven by a rotary solenoid 29. A pressure sensor 30 is provided in the compression chamber 25.

An observation image of the eye to be examined E goes through the exterior of the nozzle 11 and lens 12, and then it is transmitted through the dichroic mirror 13, so that it is directed to the CCD camera 16 after passing through the opening 14c of the alignment prism stop 14 and the lens 15. A part the alignment light receiving optical system of the alignment optical system is commonly used by the observation optical system.

In the alignment projection system, a light flux emitted from the light source 21 is transmitted through the projection lens 20, the dichroic mirror 19, the half mirror 18 and the lens 17 and reflected by the dichroic mirror 13 so as to be directed to the eye to be examined E through the interior of the nozzle 11. A light flux reflected by the cornea Ec of the eye to be examined E passes through the window having a hole 10 and the lens 12 in the alignment light receiving optical system and enters the dichroic mirror 13. A part of the light flux is transmitted through the dichroic mirror 13 and separated into two light fluxes by the prisms 14d and 14e of the alignment prism stop 14, so that the light fluxes are directed to the CCD camera 16.

Figure 4A:
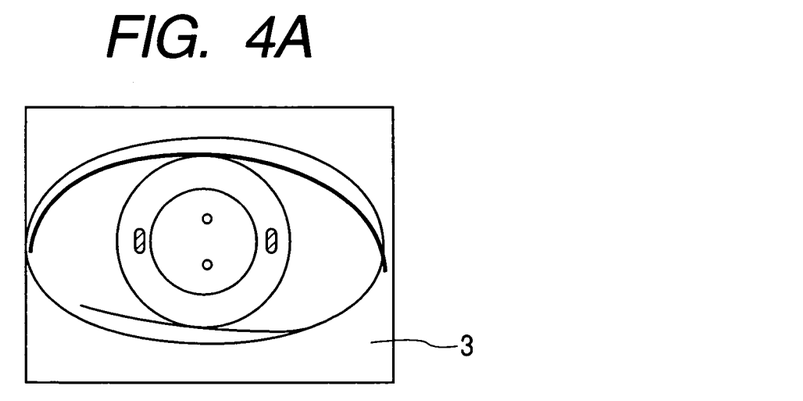
FIGS. 4A, 4B and 4C illustrates an image of an anterior ocular segment upon an alignment operation using alignment light.

In the observation optical system, the light flux passes through the central opening 14c, while in the alignment light receiving optical system, the light flux is adapted to enter the prisms 14d and 14e that transmit only light having the wavelength corresponding to the light source 21. In the left prism 14d, the light flux is refracted downwardly, while in the right prism 14e, the light flux is refracted upwardly. Thus, when in a correct operation distance, the spot images of the light source are formed as two bright points on the vertical line near the center on the CCD camera 16. The image of the anterior ocular segment is as shown in FIG. 4A.

Figure 4B:
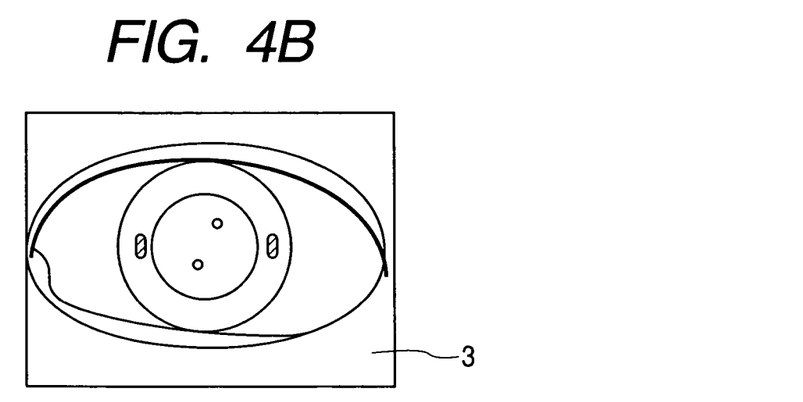
Figure 4C:
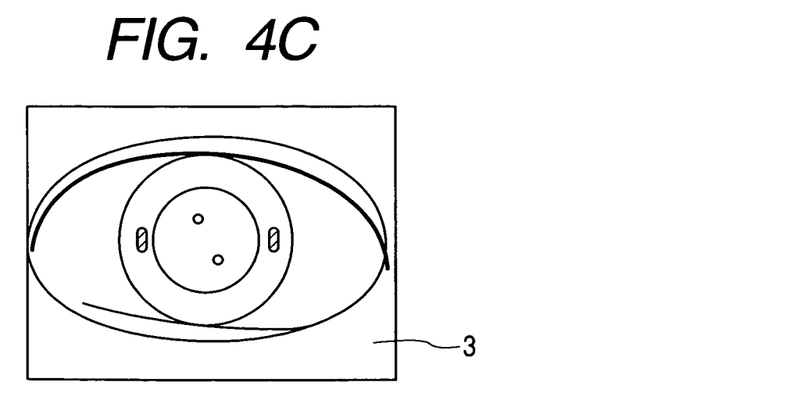

In the case that the operation distance is displaced in the backward or forward direction, the two bright points are shifted in the opposite horizontal directions relative to each other from the reference bright point positions in the correct operation distance, so that the bright points come to the positions shown in FIG. 4B or FIG. 4C. When the measuring portion 2 is displaced in the horizontal and vertical directions relative to the eye to be examined E, both of the two bright points shift in the horizontal and vertical directions in accordance with the displacement amount without changing their relative positions to each other.

The projection optical system of an optical system for detecting cornea deformation is common with the alignment projection optical system. A light flux emitted from the light source 21 is transmitted through the projection lens 20, the dichroic mirror 19, the half mirror 18 and the lens 17 and reflected by the dichroic mirror 13 so as to be directed to the eye to be examined E through the lens 12.

A light flux reflected by the cornea Ec that has been deformed passes through the window having a hole 10 and the lens 12. A part of that light flux is reflected by the dichroic mirror 13, transmitted through the lens 17 and partly reflected by the half mirror 18. The part of the light flux reflected by the half mirror 18 is directed to the photo sensor 23 through the aperture 22. The light receiving optical system is adjusted in such a way that the received light quantity of the photo sensor 23 becomes maximum when the cornea of the eye to be examined E is applanated.

In the fixation target projecting optical system, a light flux emitted from the eye fixation LED 24 is reflected by the dichroic mirror 19, transmitted by the half mirror 18 and the lens 17 and reflected by the dichroic mirror 13 so as to be directed to the eye to be examined E through the interior of the nozzle 11.

Figure 5:
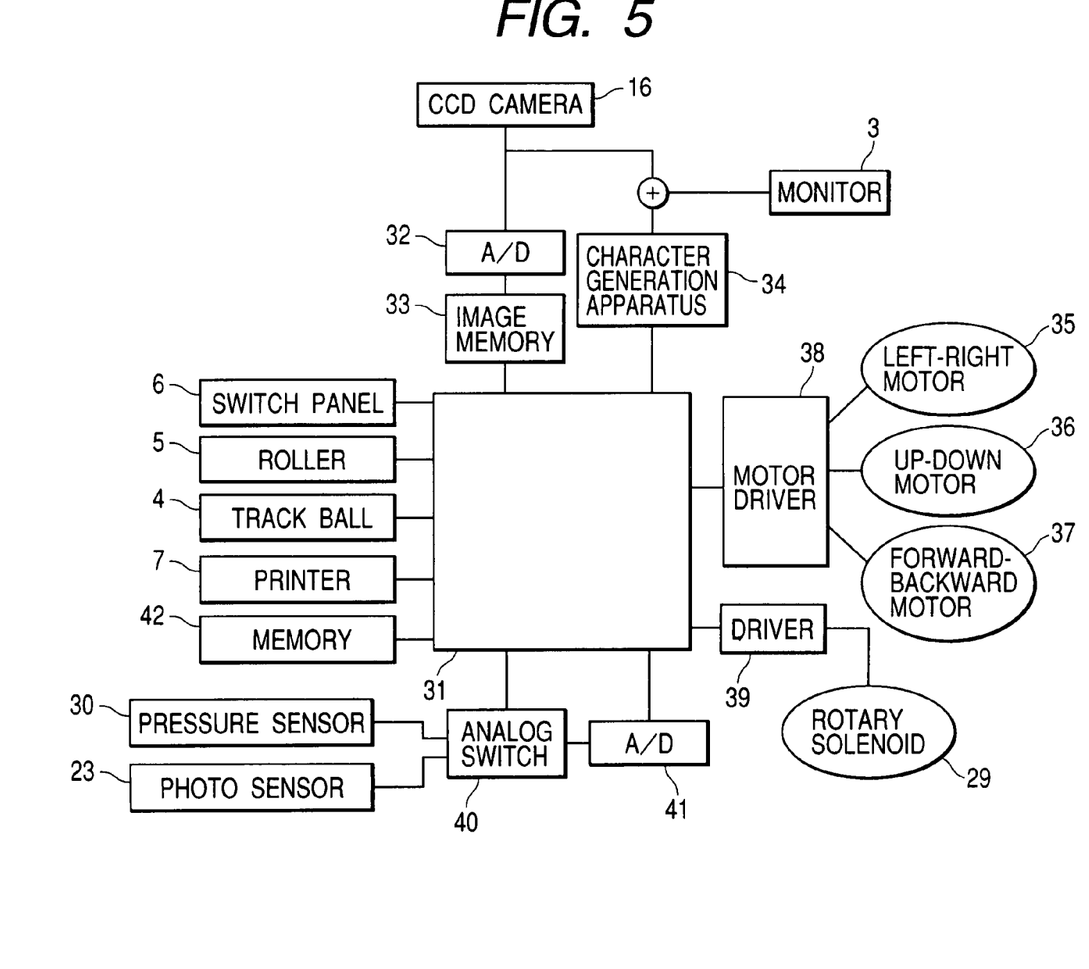
FIG. 5 is a circuit block diagram of an electric system of an non-contact tonometer.

FIG. 5 is a circuit block diagram of the electric system of this non-contact tonometer. A measurement switch, the switch panel 6, rotary encoders built in the track ball 4 and the roller 5, and the printer 7 for printing measurement results are connected to ports of a CPU 31.

An image signal representing an image of the anterior ocular segment captured by the CCD camera 16 is converted to digital data by an A/D converter 32 and stored in an image memory 33. The CPU performs image processing for extracting bright points for alignment based on the image data stored in the image memory 33 to detect alignment. The image signal representing the image of the anterior ocular segment is synthesized with a signal from a character generation apparatus 34, so that an image of the anterior ocular segment and measured values etc. are displayed on the monitor 3. A left-right motor 35, an up-down motor 36 and a forward-backward motor 37 are connected to a motor driver 38, so that the motors are driven by commands from the CPU 31 in accordance with entry from the rotary encoders of the track ball 4 or the roller 5, or in accordance with displacement in alignment when under the auto-alignment operation.

A rotary solenoid is connected to a driver 39 so as to be driven by a command from the CPU 31. The output from the pressure sensor 30 and the output from the photo sensor 23 are input to an analogue switch 40. The analogue switch 40 outputs a signal selected by the CPU 31 from among the two input signals to an A/D converter 41. The outputs of the analogue switch 40 and the A/D converter 41 are connected to the CPU 31. In addition, a memory 42 is connected to the CPU 31.

Figures 6, 6A:
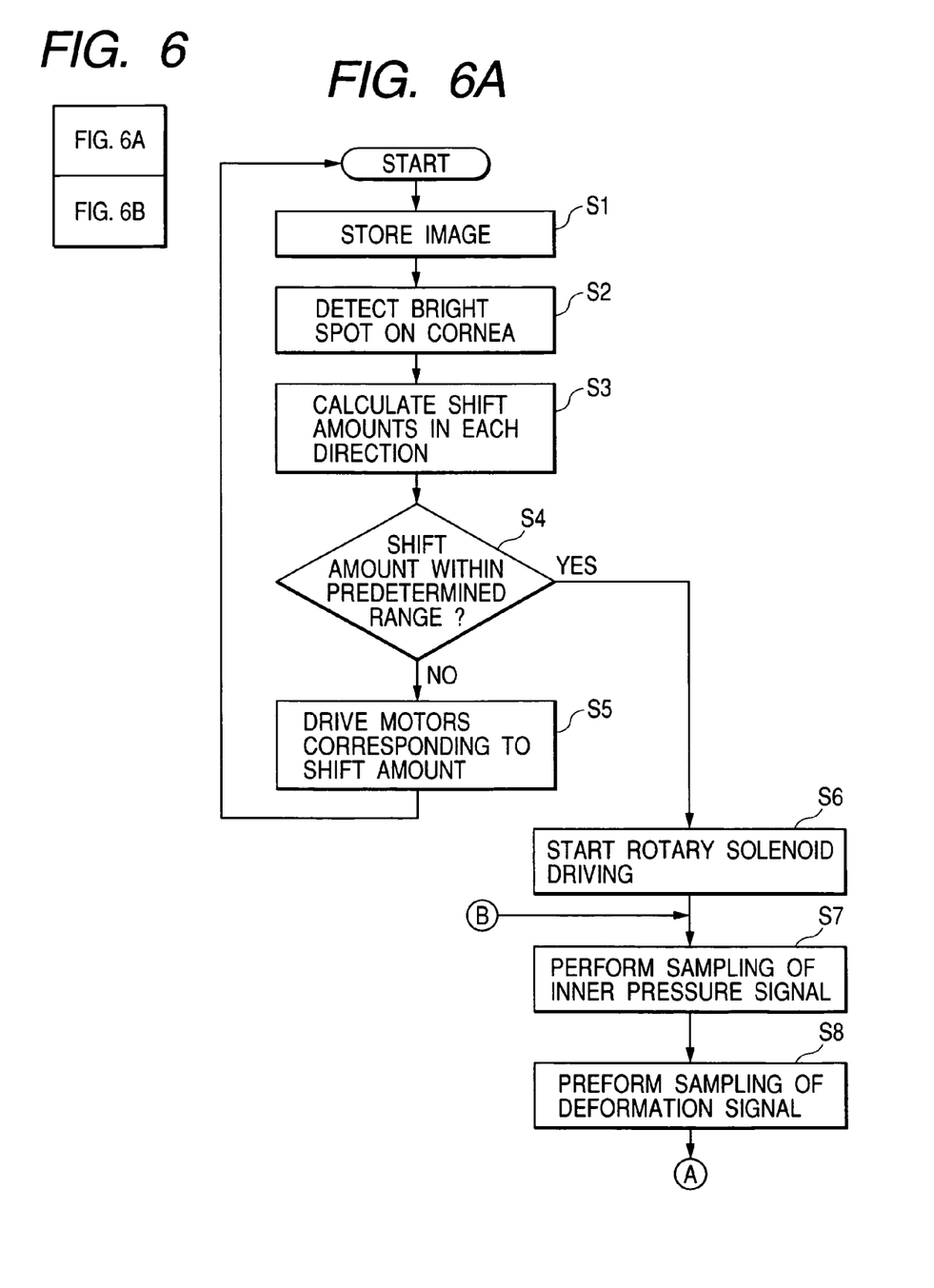
FIG. 6 is comprised of FIGS. 6A and 6B showing flow charts of an operation of measuring intraocular pressure.
Figure 6B:
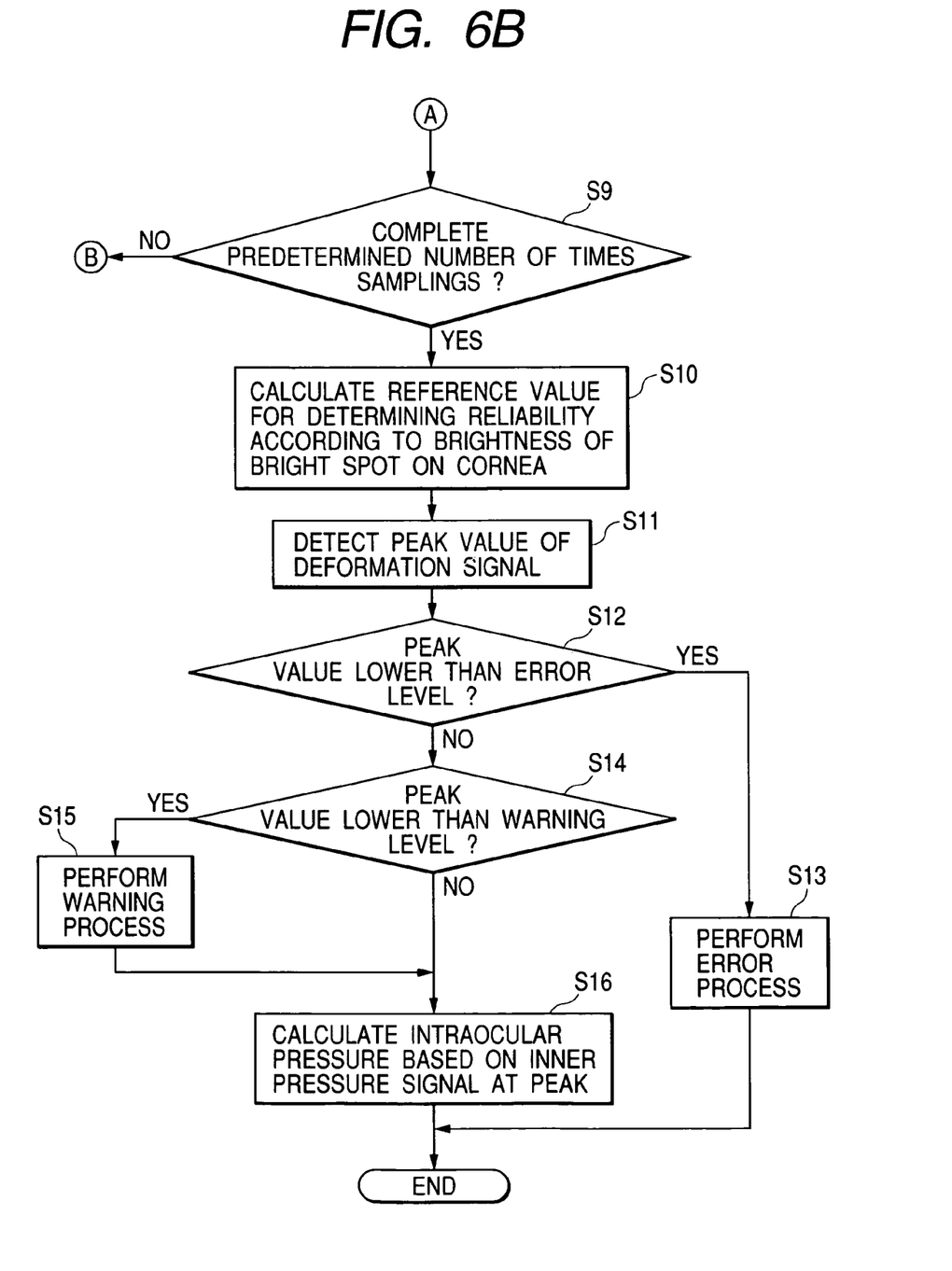

FIGS. 6A and 6B are flow charts of the measuring operation in the non-contact tonometer having the above-described structure. First, the examiner should drive the left-right, up-down and forward-backward motors 35, 36 and 37 by operating the track ball 4 and the roller 5 until two bright points for alignment are seen on the monitor 3 to attain rough alignment of the eye to be examined E and the measuring portion 2. After that, the examiner should depress the start switch in the switch panel 6 to cause the auto-alignment operation to start.

As the auto-alignment operation, in step S1 an image signal representing an image of the anterior ocular segment of the eye to be examined E captured by the CCD camera 16 is converted to digital data by the A/D converter and stored in the image memory 33. Next, in step S2, the CPU 31 performs image processing on the image data that was stored in the image memory in step S1 to detect the positions of the two bright points for alignment.

In step S3, shift amounts (i.e. misalignment amounts) with respect to the horizontal, vertical and depth directions are respectively calculated based on the detected positions of the bright points. In step S4, it is determined whether or not the misalignment amounts are within a predetermined range. When it is determined that the misalignment amount is out of the range, the process proceeds to step S5, in which the left-right, up-down and forward-backward motors 35, 36 and 37 are driven in accordance with the misalignment amounts to move the measuring portion 2. The auto-alignment operation from step S1 to step S5 is repeated until it is determined in step S4 that the misalignment amounts are within the predetermined range that allows measurement.

When the auto-alignment is completed, the process proceeds to step S6, in which driving of the rotary solenoid 29 via the driver 39 is started by a command from the CPU 31. As the driving is started, the piston 28 moves in the cylinder 26 so as to pump air to the compression chamber 25 that is connected to the cylinder 26 via the tube 27. The air supplied to the compression chamber 25 is compressed and blown to the eye to be examined E through the nozzle 11, so that the cornea Ec starts to deform.

In steps S7 and S8, sampling of the inner pressure signal indicative of a pressure in the interior of the compression chamber and a deformation signal indicative of the deformation of the cornea is performed. The sampling of the inner pressure signal and the deformation signal is performed a set number of times at a predetermined sampling frequency, and the results are stored in the memory 42 in time series order. In step S7, sampling of the inner pressure signal is performed. The CPU31 switches the input of the analogue switch 40 so that the signal of the pressure sensor 30 is input to the A/D converter 41 so as to have the signal A/D-converted. The obtained digital data is stored in memory 42. In step S8, sampling of the cornea deformation signal is performed. The CPU31 switches the input of the analogue switch 40 so that the signal of the photo sensor 23 is input to the A/D converter 41 so as to have the signal A/D-converted. The obtained digital data is stored in memory 42.

When it is determined in step S9 that a predetermined number of times of the sampling has been completed, the process proceeds to step S10. In step S10, the brightness of the bright points for alignment detection is determined based on the image data of the anterior ocular segment at the time the alignment is attained stored in the image memory in step S1, and an error level and a warning level are calculated using a conversion formula prepared in advance.

In step S11, the peak value of the deformation signal is detected based on the data of the deformation signal stored in the memory 42. In step S12, the error level calculated in step S10 and the peak data of the photo sensor 23 are compared. In the case that the peak value is equal to or smaller than the error level, the process proceeds to step S13, in which an error process is performed. In the error process, an error indication or the like is displayed on the monitor 3 and the series of measurement operations are terminated.

In the case that the peak value is larger than the error level, the process proceeds to step S14. In step S14, the warning level calculated in step S10 and the peak data of the photo sensor 23 are compared. In the case that the peak value is equal to or smaller than the warning level, the process proceeds to step S15, in which a warning process is performed. In the warning process, a warning data flag is set.

After that, the process proceeds to step S16, in which the intraocular pressure of the eye to be examined is calculated based on the data of the inner pressure signal at the time the deformation signal assumes the peak, using a conversion formula prepared in advance. The measured value is displayed on the monitor 3. In addition, in the case that the warning flag is set, a low reliability mark is annexed to the measured value. Thus, a series of measurement operations are terminated.

Figure 7:
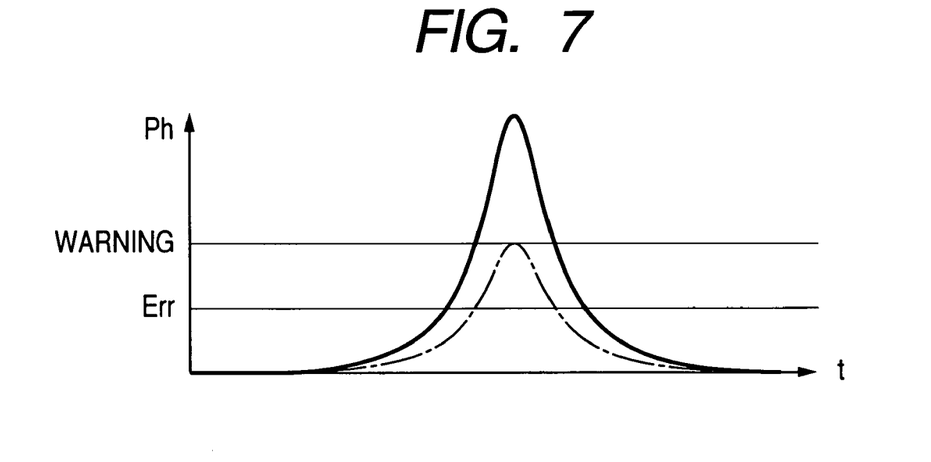
FIG. 7 is a graph showing a photosensor output and levels of reliability.

FIG. 7 is a graph showing the relation of outputs of the photo sensor 23, the warning level and the error level. In the graph, the axis of abscissa represents elapsed time and the axis of ordinate represents the output value of the photo sensor 23. The solid curve shows an output upon a normal measurement performed on a normal eye, while the dashed curve shows an output upon a normal measurement performed on a cornea having a reflectance of half the reflectance of a normal eye.

If a level "Err" equal to one forth of the peak with the normal eye is set as the error level and a level "Warning" equal to half of the peak with the normal eye is set as the warning level, in the case that a cornea having a reflectance half the reflectance of the normal eye is measured, the output reaches no more than the warning level even when the measurement is normally performed. Consequently, it will be always judged that the measurement is of low reliability. In addition, when the output is reduced to half due to misalignment or other reasons, it will be judged that the measurement is erroneous, in spite that it is of a warning level in reality.

Figure 8:
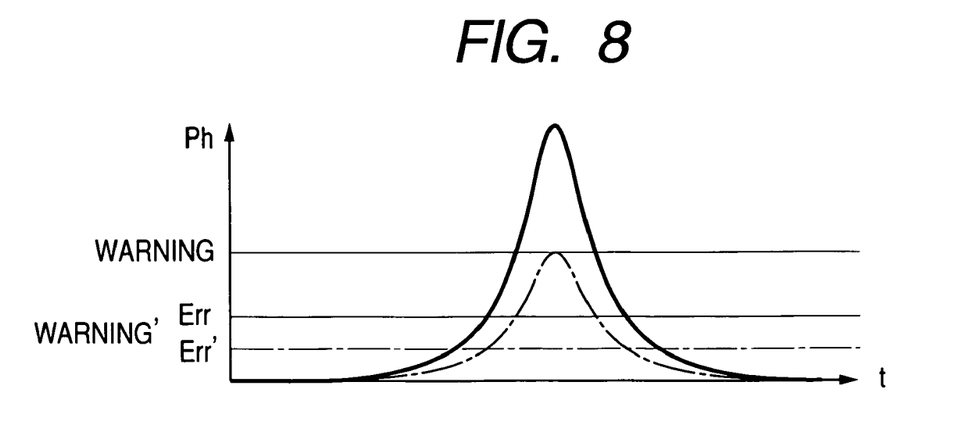
FIG. 8 is a graph showing a photosensor output and levels of reliability.

In view of the above situation, the value of the output at the peak for the eye to be examined is estimated based on the quantity of light received by the alignment detection means, and for a cornea with a low reflectance, the error level and the warning level are changed to "Err'" and "Warning'" respectively in a relative manner as shown in FIG. 8. Thus, variations in determination of reliability due to differences in the reflectance of corneas Ec can be reduced.

As has been described in the foregoing, in the non-contact tonometer according to the present invention, a reference value used for determining reliability of measurement is changed in accordance with the quantity of light received by the alignment detection means. With this feature, stable determination of reliability can be realized irrespective of differences in the reflectance of eyes to be examined.

What is claimed is:

1. A non-contact tonometer comprising:
    an alignment light source for emitting a light flux for alignment of a cornea of an eye to be examined;
    a projection optical system for projecting the light flux from the alignment light source onto the cornea of the eye to be examined;
    image capture means for sensing, after completing the alignment between the cornea of the eye to be examined and the non-contact tonometer, an image obtained from a reflected alignment light flux which is the light flux projected onto and reflected by the cornea of the eye to be examined;
    a cornea deformation means for deforming the cornea of the eye to be examined by blowing pressurized air onto the cornea of the eye to be examined;
    an intraocular pressure measurement light source for emitting a measurement light flux for measurement of an intraocular pressure of the eye to be examined;
    the projection optical system further projecting the measurement light flux from the intraocular pressure measurement light source onto the cornea of the eye to be examined;
    intraocular pressure measurement light receiving means for detecting a reflected measurement light flux which is the measurement light flux projected onto and reflected from the cornea of the eye to be examined; and a CPU configured to determine reliability of measurement of an output signal which is output from the intraocular pressure measurement light receiving means on the basis of an intensity of the image, at a time of completing the alignment, sensed by the image capture means, and to execute an error processing and a warning processing in accordance with the determined reliability of measurement, wherein the CPU executes said warning processing by adding a reliability mark to the output signal in a case that an output value of the output signal from the intraocular pressure light receiving means exceeds a predetermined reference value, and wherein the CPU executes said error processing by generating an error indication in a case that the output value of the signal from the intraocular pressure light receiving means is equal to or smaller than said predetermined reference value.

* * * * *